US008511549B2

(12) United States Patent
Steimle et al.

(10) Patent No.: US 8,511,549 B2
(45) Date of Patent: Aug. 20, 2013

(54) ANALYSIS SYSTEM FOR ANALYZING BIOLOGICAL SAMPLES, METHODS, AND COMPUTER PROGRAM PRODUCT THEREOF

(75) Inventors: Anton Steimle, Rueti (CH); Bernhard Von Allmen, Seengen (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 167 days.

(21) Appl. No.: 12/883,271

(22) Filed: Sep. 16, 2010

(65) Prior Publication Data

US 2011/0220715 A1   Sep. 15, 2011

(30) Foreign Application Priority Data

Sep. 17, 2009   (EP) ..................................... 09170598

(51) Int. Cl.
*G06K 5/00*        (2006.01)
(52) U.S. Cl.
USPC ............ 235/380; 235/375; 235/487; 235/382
(58) Field of Classification Search
USPC .................. 235/380, 375, 376, 487, 485, 382
See application file for complete search history.

(56) References Cited

U.S. PATENT DOCUMENTS

| | | | |
|---|---|---|---|
| 2006/0089855 A1* | 4/2006 | Holland et al. ................... 705/2 |
| 2007/0078610 A1 | 4/2007 | Adams et al. | |
| 2009/0051526 A1 | 2/2009 | Spear et al. | |
| 2009/0094529 A1 | 4/2009 | Gonzalez et al. | |
| 2009/0100166 A1* | 4/2009 | DeAnna et al. ............... 709/223 |
| 2009/0259493 A1* | 10/2009 | Venon et al. ..................... 705/3 |
| 2009/0299762 A1* | 12/2009 | Martin et al. ..................... 705/2 |
| 2009/0307137 A1* | 12/2009 | White et al. .................... 705/51 |
| 2010/0042351 A1* | 2/2010 | Covey et al. ................. 702/108 |

FOREIGN PATENT DOCUMENTS

| | | |
|---|---|---|
| EP | 1691186 A1 | 8/2006 |
| EP | 1840576 A2 | 10/2007 |
| WO | 2004102163 A2 | 11/2004 |
| WO | 2005031366 A1 | 4/2005 |
| WO | 2009085534 A1 | 7/2009 |

OTHER PUBLICATIONS

Timm, et al., "Concept and Specification of LIMS for pharmacokinetic studies", Laboratory automation and information management, Elsevier Science Publishers, vol. 32, No. 1, May 1, 1996, pp. 7-22.

* cited by examiner

*Primary Examiner* — Edwyn Labaze
(74) *Attorney, Agent, or Firm* — Dinsmore & Shohl LLP

(57) ABSTRACT

An analysis system for analyzing biological samples, such as body fluids, methods implemented by the analysis system, and a computer program product for implementing the analysis system are disclosed. The system may include first and second lab devices, at least one of the lab devices may have a user identification component for identifying a user, a device identification component for identifying the lab device, and an interface component for sending a user identifier of the identified user and a device identifier of the lab device. The system may include a server computer having a server interface component for receiving the user identifier and the device identifier, and a processing component for determining a step of a workflow to be executed by the identified user, wherein the server interface component is operable to send a signal being indicative of a determined workflow to the lab device identified by the device identifier.

17 Claims, 10 Drawing Sheets

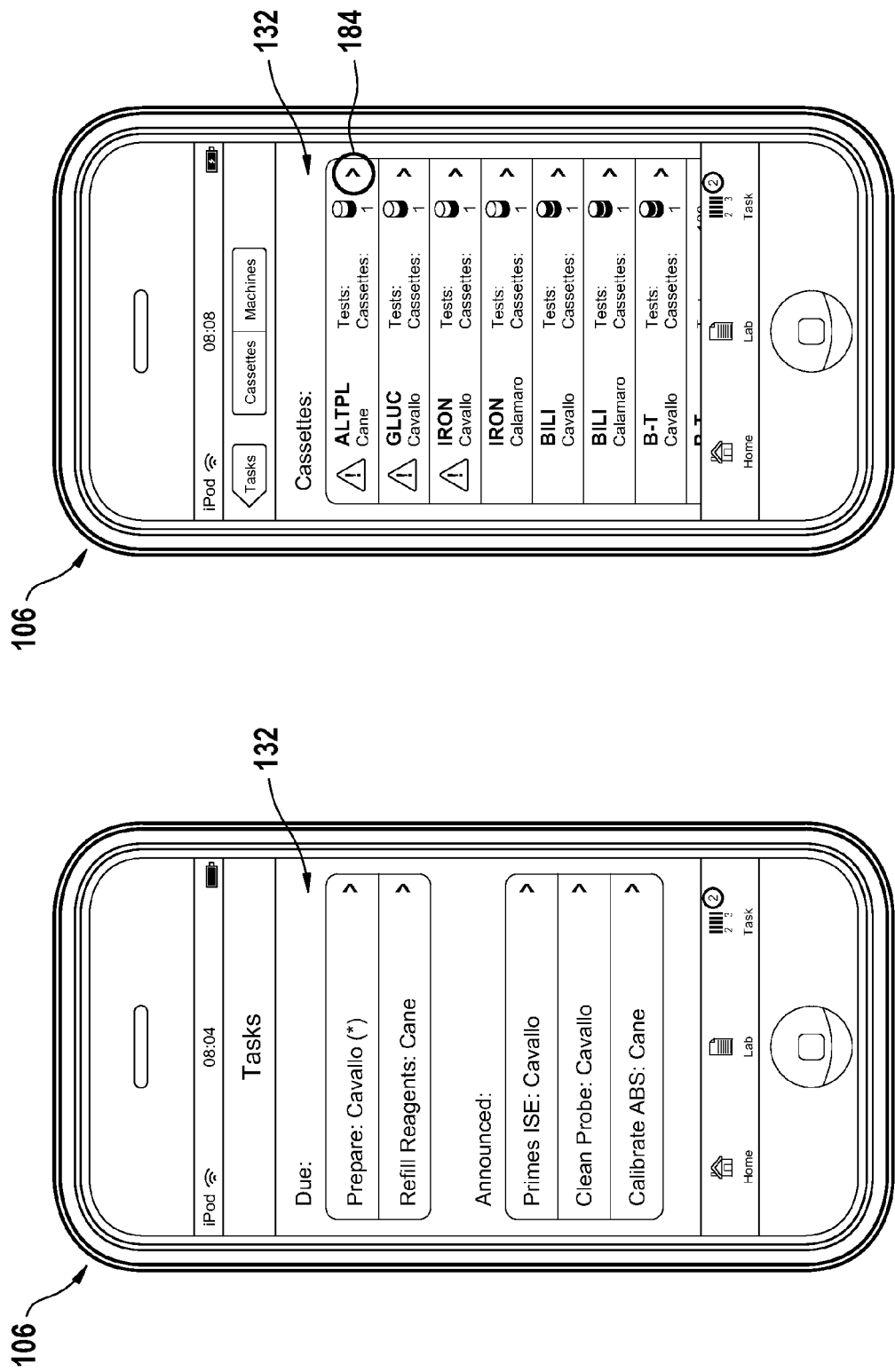

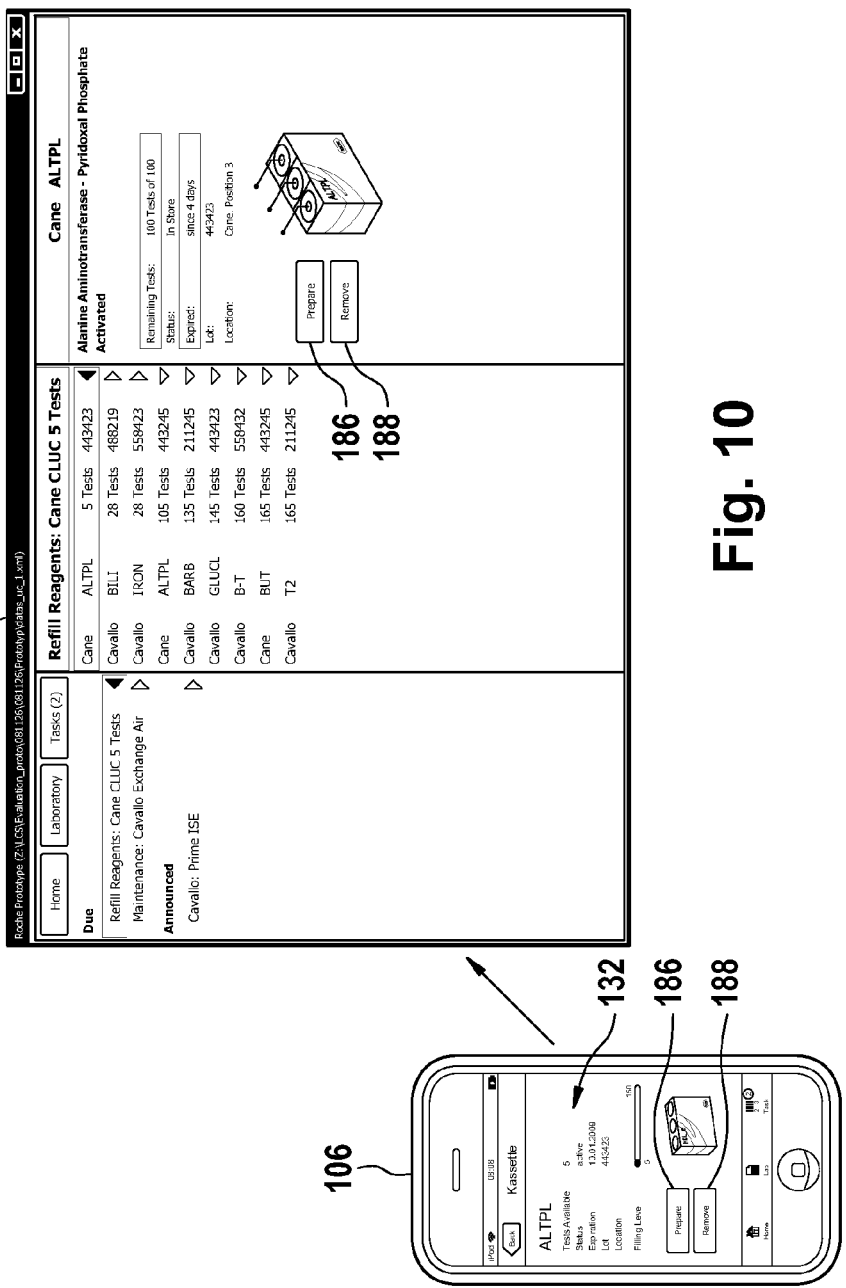

| Refill Reagents: Cane CLUC 5 Tests | | | | Cane ALTPL |
|---|---|---|---|---|
| Cavallo | BILI | 28 Tests | 488219 | Alanine Aminotransferase - Pyridoxal Phosphate |
| Cavallo | IRON | 28 Tests | 558423 | Activated |
| Cane | ALTPL | 105 Tests | 443245 | |
| Cavallo | BARB | 135 Tests | 211245 | Remaining Tests: 100 Tests of 100 |
| Cavallo | GLUCL | 145 Tests | 443423 | Status: In Store |
| Cavallo | B-T | 160 Tests | 558432 | Expired: since 4 days |
| Cane | BUT | 165 Tests | 443245 | Lot: 443423 |
| Cavallo | T2 | 165 Tests | 211245 | Location: Cane, Position 3 |
| Cane | ALTPL | 105 Tests | 443423 | |

Tasks (2)

Due
Maintenance: Cavallo Exchange Air

Announced
Cavallo: Prime ISE

Done
Refill Reagents: Cane ALTPL 5 Tests

[Prepare] [Remove] — 186, 188

ANALYSIS SYSTEM FOR ANALYZING BIOLOGICAL SAMPLES, METHODS, AND COMPUTER PROGRAM PRODUCT THEREOF

CROSS-REFERENCE TO RELATED APPLICATIONS

This application claims the benefit of European application EP09170598.8, filed Sep. 17, 2009, which is herein incorporated fully by reference.

TECHNICAL FIELD

The present disclosure relates to analyzing biological samples, and in particular to an analysis system for analyzing biological samples, such as body fluids, methods implemented by the analysis system, and a computer program product for implementing the analysis system.

BACKGROUND

Various automatic analyzers are known for analyzing biological samples, such as in vitro analyzers. Although such analyzers are suitable for their intended purposes, improvements thereof are still needed.

SUMMARY

In one embodiment, an analysis system for analyzing biological samples comprising a first lab device, a second lab device, and a server computer is disclosed. At least one of the first lab device and the second lab device may comprise a user identifier for identifying the user, a device identifier for identifying the lab device, and an interface component which sends the user identifier and the device identifier to the server computer. The server computer may comprise a server interface component which receives the user identifier and the device identifier, and a processing component which determines a step of a workflow to be executed by the identified user, wherein the server interface component is operable to send a signal being indicative of the determined step to the lab device identified by the device identifier.

In another embodiment, a method implemented by an analysis system for analyzing biological samples is disclosed. The method may comprise identifying a user of at least one of a first lab device and a second lab device, sending a user identifier and a device identifier of the at least one of the first and second lab devices to a server computer, determining a step of a workflow using the server computer by the user identifier and the device identifier of the at least one of a first and second lab devices, and sending a signal comprising of the determined step from the server computer to at least one of the first and second lab devices.

In still another embodiment, another method implemented by an analysis system for analyzing biological samples is disclosed. The method may comprise identifying a user by at least one of a first lab device and a second lab device, sending a user identifier and a device identifier of the at least one of the first and second lab devices to a server computer, and determining a step of a workflow with the server computer using the user identifier and the device identifier. The method may further comprise sending a signal comprising the determined step from the server computer to at least one of the first and second lab devices, and receiving the signal on at least one mobile device. The signal may comprise the at least one determined step of the workflow, at least one of the lab devices to be used for execution of the at least one step of the workflow, position information indicating a geographic or topological location of the lab device to be used for the execution of the at least one determined step, and one or more steps of the workflow to be executed at an unconnected lab device. The unconnected lab device may comprise a lab device that is not coupled to the server computer.

These and other advantages and novel features of the various embodiments disclosed herein will become more apparent from the following detailed description when considered in conjunction with the drawings.

BRIEF DESCRIPTION OF THE DRAWINGS

In the drawings like structure is indicated with like reference numerals and in which:

FIG. 7 depicts an example of a screen image that is displayed on a mobile device after receipt of the signal indicating the requirement for a refill in accordance with another embodiment;

FIG. 8 depicts the mobile user device of FIG. 7 after the user has entered a navigation command in accordance with yet another embodiment;

FIG. 9 illustrates the mobile user device of FIGS. 7 and 8 after the user has entered a further navigation command in accordance with another embodiment;

FIG. 10 depicts a screen image being displayed on a monitor of one of the analyzer control computers in accordance with one embodiment;

FIG. 11 depicts the mobile user device of FIG. 9, in accordance with one embodiment;

FIG. 12 depicts a change to the screen image of FIG. 10 after a task has been completed in accordance with yet another embodiment.

DETAILED DESCRIPTION

Figure 1:
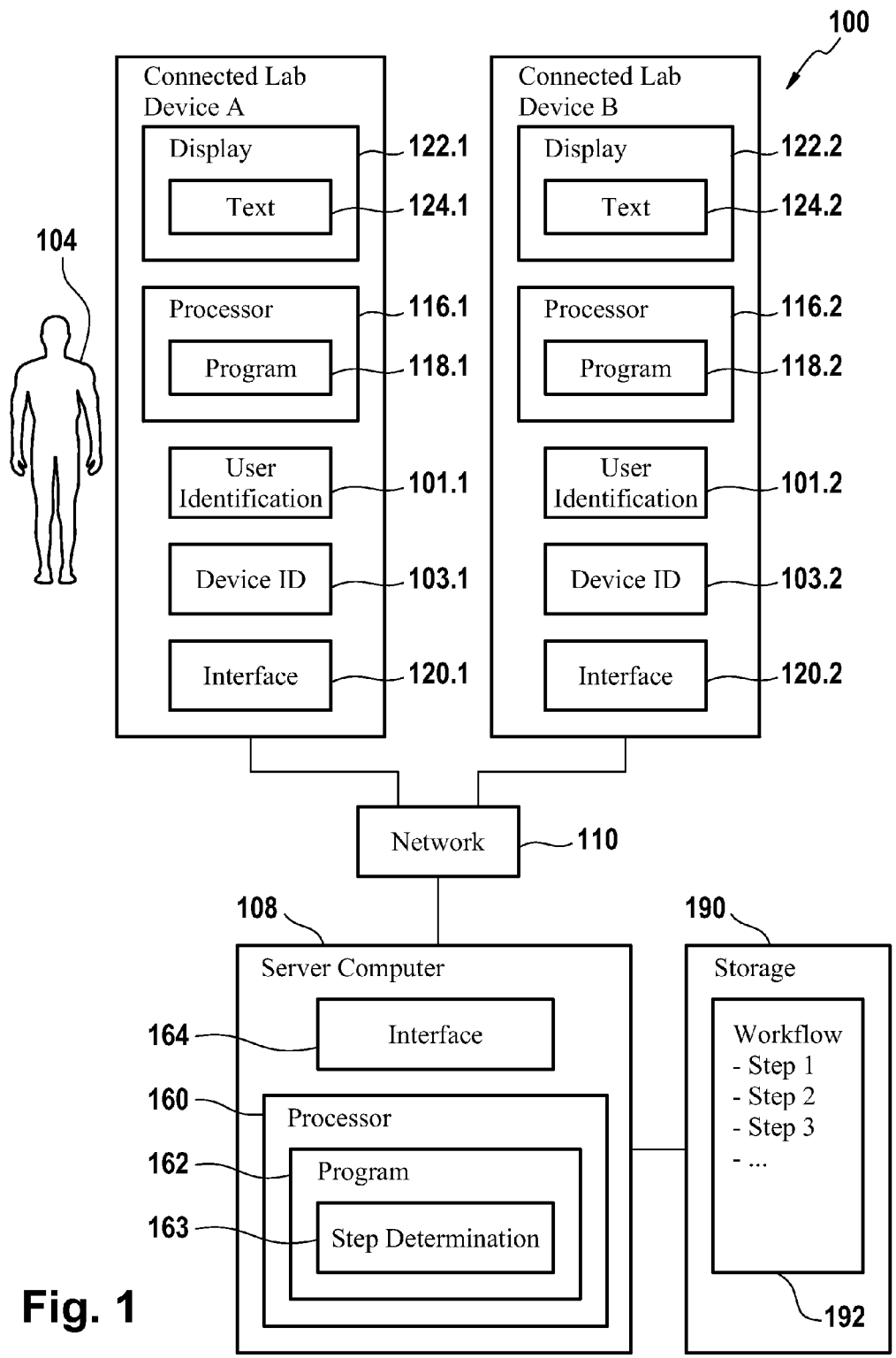
FIG. 1 depicts a block diagram of the analysis system in accordance with one embodiment.

In the following description of the preferred embodiments like elements will be designated by identical reference numerals.

The term "analyzer" as used herein encompasses any apparatus that can induce a reaction of a sample with a reagent for obtaining a measurement value. For example, the analyzer measures light absorption, fluorescence, electrical potential or other physical or chemical characteristics of the reaction to provide the measurement data.

The term 'workflow' as used herein encompasses any task that comprises a number of predefined steps, such as for maintenance or operation of the analysis system or one of its system components.

The term 'step of a workflow' as used herein encompasses any activity belonging to a workflow. The activity can be of an elementary or complex nature and is typically performed at or by means of a single lab device.

The term 'analytical data' as used herein encompasses any data that is descriptive of a result of an analysis performed by the automatic analyzer and an identifier of the biological sample that has been analyzed, and may further comprise the order number. In case of a calibration, the analytical data comprises the calibration result, i.e. calibration data. In particular, the analytical data may comprise an identifier of the sample for which the analysis has been performed and data being descriptive of a result of the analysis, such as measurement data.

The term 'lab device' as used herein encompasses any analyzer and any other laboratory device related to a sample to be analyzed or a receptacle of a sample, analytical adjuvant material, reagent, wash buffer, auxiliary liquid, such as a pipette, pipette tip, or bulb, and including pre-analytical devices, such as decapper devices, sample preparation and distribution systems, post-analytical devices, and in particular, automated sample storage devices. The execution of a step of a workflow involves usage of such a lab device.

The term 'connected lab device' as used herein encompasses any lab device that is coupled to a server computer, in particular any lab device that has a network interface for communicating with a server computer or other communication means for establishing a communication channel for data exchange with a server computer, such as via a wireless communication channel or a Local Area Network (LAN).

The term 'unconnected lab device' as used herein encompasses any lab device that is not coupled to a server computer, in particular, any lab device that does not have a network interface for communicating with a server computer, such as a refrigerator or a shelf for stocking reagents or samples.

The term 'mobile device' as used herein encompasses any mobile electronic appliance having an interface for communicating with a server computer, in particular, any handheld battery powered mobile appliance, such as a mobile phone, a smart phone, a personal digital assistant (PDA) or another electronic appliance having a wireless interface for establishing a communication link with a server computer such as over a wireless digital cellular telecommunications network or another wireless communication channel.

The embodiments of the present disclosure relate to improved analysis systems and improved computer-implemented methods and computer program products. The present disclosure more particularly relates to an analysis system for analyzing biological samples.

In accordance with one embodiment, an analysis system for analyzing biological samples is provided comprising at least a first and a second lab device, where at least one of the lab devices have a user identifier component for identifying a user, a device identifier component for identifying the lab device, and an interface component for sending the user identifier and the device identifier to a server computer. The analysis system may also comprise a server computer having a server interface component for receiving the user identifier and the device identifier, a processing component for determining a step of a workflow to be executed by the identified user, wherein the server interface component is operable to send a signal being indicative of the determined step of the workflow to the device identified by the device identifier.

Embodiments of the present disclosure are particularly advantageous as the user is informed of one or more steps of a workflow to be executed by that user from the server computer upon logging in with at least one of the first or second lab devices. This enables a highly convenient and efficient analysis system.

In accordance with another embodiment, completion of the execution of a step of the workflow is signaled to the server computer. For example, the user can use an unconnected lab device for execution of the determined step and then enter an acknowledgement into a connected lab device such that completion of the execution is signaled from the connected lab device to the server computer.

In accordance with yet another embodiment, the server computer comprises a database configured to assign a first set of steps of the workflow to the first lab device and assign a second set of steps of the workflow to the second lab device. The processing component of the server computer generates a message when the determined step is not assigned to the identified lab device in the database. For example, the message is sent from the server computer to the identified lab device indicating another one of the lab devices to which the determined step is assigned, and can be used by the user for execution of the determined step.

In another embodiment, the analysis system further comprises at least one mobile device. The mobile device can receive the signal being indicative of the determined step of the workflow. This signal is also indicative of the lab device to be used for execution of the determined step of the workflow. This is particularly convenient and efficient as the integration of at least one mobile device into the analysis system allows ubiquitous operation of the analysis system.

In another aspect, a method for analyzing biological samples is provided. The method comprises the steps of identifying a user by at least one of a first lab device and second lab device, sending a user identifier and a device identifier of at least one of the first lab device and the second lab device to a server computer, determining a step of a workflow by the server computer using the user identifier and the device identifier, and sending a signal being indicative of the determined step from the server computer to the at least one of the lab devices.

The workflow can be stored on the server computer or on another device, such as a connected lab device and/or mobile device. The workflow can be static or it can be dynamically generated and/or adapted in response to events, triggers or user actions that require the modification of the workflow. The execution of the workflow may be tracked by the server computer, the connected lab device, and/or the mobile device. The determination of the step of the workflow by the server computer can be performed using a workflow management system that runs on the server computer or on another server computer that is connected to the network.

In accordance with yet another embodiment, the mobile device of the analysis system may receive a signal being indicative of the at least one determined step of the workflow and also being indicative of at least one of the lab devices to be used for execution of this step. In addition, the signal can be indicative of the position of the lab device to be used for execution. The position information can comprise an indication of the geographic and/or topological location of the lab device. For example, the position information may be provided as a laboratory room number for indicating the laboratory room in which the lab device is located.

In accordance with an embodiment, the analysis system comprises at least one unconnected lab device that is not coupled to the server computer, such as a refrigerator, reagent shelf, or another lab device that does not have electronic components. In this instance, the signal that is received by the mobile device can be indicative of one or more steps of the workflow to be executed at the unconnected lab device.

In accordance with another embodiment, the signal received from the server is indicative of a priority of the steps of the workflow. In response to receipt of the signal by the mobile device or the lab device, the steps are displayed in the prioritized order given by the signal.

In accordance with an embodiment, the signal that indicates the determined step of the workflow is sent from the server computer in a push or pull operation to the lab device or mobile device.

In accordance with another embodiment, the user identification is performed by a user login operation, by means of an RFID method and/or by means of a chip card. In particular, the mobile device can be used for the user identification, as the mobile device typically signals the user's telephone number when a communication channel is established. The user's telephone number can be used for the user's identifier. For example, the mobile device can comply with a mobile digital telecommunication standard, such as a GSM standard, such that the mobile device has an integrated card reader for a so-called subscriber identity module (SIM) card. The data that is stored on the SIM card can be used for the user identifier.

In still another embodiment, a computer program product comprising executable program instructions for execution by a server computer of the methods described throughout this disclosure. Reference hereafter is now made to the figures, which depict various illustrated embodiments.

FIG. 1 depicts a block diagram of an analysis system 100. The analysis system 100 comprises various analyzers being coupled to analyzer control computers that control operation of their respective analyzer. An analyzer can be coupled to an analyzer control computer that controls operation of the analyzer. Depending on the implementation the analyzer or the analyzer control computer is coupled to the server computer 108 via the network 110; hence, the analyzer and/or the analyzer control computer can constitute a connected lab device. In the embodiment considered here, the analysis system 100 has a connected lab device A and a connected lab device B. The connected lab device A has at least one processor 116.1 for execution of program instructions 118.1. The connected lab device A has a network interface 120.1 for coupling the connected lab device A to the network 110, in particular, in order to enable communication with a server computer 108.

The network 110 can be a cable-based network, such as a local area network, or a wireless network, such as a WIFI, GSM, UMTS or other wireless digital network. In particular, the network 110 can implement the Internet protocol (IP), in particular mobile IP. For example, the network 110 may comprise a combination of cable-based and wireless networks. The connected lab device A may have a display, such as a computer monitor 122.1 for displaying a screen image 124.1 that may include a textual output. Further, the connected lab device A has a user identification component 101.1 and a device identification component 103.1, such as a user identifier and a device identifier.

The user identification component 101.1 serves for identification of a human user 104, such as a laboratory assistant. The user identification component 101.1 may comprise the user's 104 entry of his or her user name and password. Alternatively, or in addition, the user identification component 101.1 can implement an RFID method for determining the user's 104 identity by means of an RFID chip card of that user. As an alternative or in addition, the user identification component 101.1 can be communicated/created using a biometric method, such as fingerprint identification. In this instance, the user identification component 101.1 comprises a sensor for sensing the user's 104 respective biometric features, such as a fingerprint sensor.

The device identification component 103.1 can be a protected storage area of the connected lab device A in which a unique device identifier for identification of the device is stored. This device identifier can be a serial number, such as a globally unique identifier (GUID) that is assigned to the connected lab device A during its production. The user identifier may be unique within the analysis system and may be assigned to the connected lab device A by an administrator of the analysis system. Alternatively, the device identifier (ID) is not permanently stored by the device identification component 103.1 but the device identifier is computed by the device identification component 103.1 each time an identification of the connected lab device A is required. The computation of the device ID can be executed by the device identification component 103.1 using a predefined algorithm, such as a cryptographic algorithm.

The connected lab device B of the analysis system 100 may have a design that is analogous to the connected lab device A. Thus, the connected lab device B may have user identification component 101.2, a device identification component 103.2, and a processor 116.2 for execution of program instructions 118.2, a monitor 122.2 for displaying a screen image 124.2 and a metric interface 120.2 corresponding to the respective components of the connected lab device A. The analysis system 100 can have a plurality of additional connected lab devices that are also coupled to the server computer 108 over the network 110.

The server computer 108 has a processor 160 for execution of program instructions 162, and a network interface 164 for coupling the server computer 108 to the network 110. The program instructions 162 comprise a program module 163 for determination of a step of workflow 192 that is stored in a storage component 190 that is coupled to the server computer 108. The storage component 190 can form an integral part of the server computer 108 or it can be a separate component such, as a database server that is either directly coupled to the server computer 108 or via the network 110.

The workflow 192 comprises a variety of steps, such as step 1, step 2, step 3, etc. In addition, other workflows can be stored in the storage 190. In operation, the user 104 selects one of the connected lab devices of the analysis system 100, such as connected lab device A. By operation of the user identification component 101.1, the user 104 is identified, such as by an entry of a user identifier. The user's 104 identifier and the device identifier of the connected lab device A provided by the device identifier component 103.1 are sent from the interface 120.1 of the connected lab device A to the server computer 108 via the network 110. This invokes the execution of the program module 163 that determines a step of the workflow 192 depending on both the user identifier and the device identifier received from the connected lab device A. For example, the program module 163 queries a database in which the workflow 192 is stored using the user identifier and/or the device identifier as a search term in order to retrieve a step of the workflow that is assigned to that user.

By execution of the program module 163, the processor 160 generates a signal that is indicative of the determined step of the workflow. This signal is sent from the server computer 108 via the network 110 to the connected lab device identified by the device identifier, i.e. connected lab device A. In response to receipt of this signal by the connected lab device A, the execution of the program instructions 118.1 is invoked such that the screen image 124.1 is displayed on the monitor 122.1 including the textual output being descriptive of the determined step. Consequently, the user 104 is informed regarding the step of the workflow 192 to be executed by that user.

Figure 2:
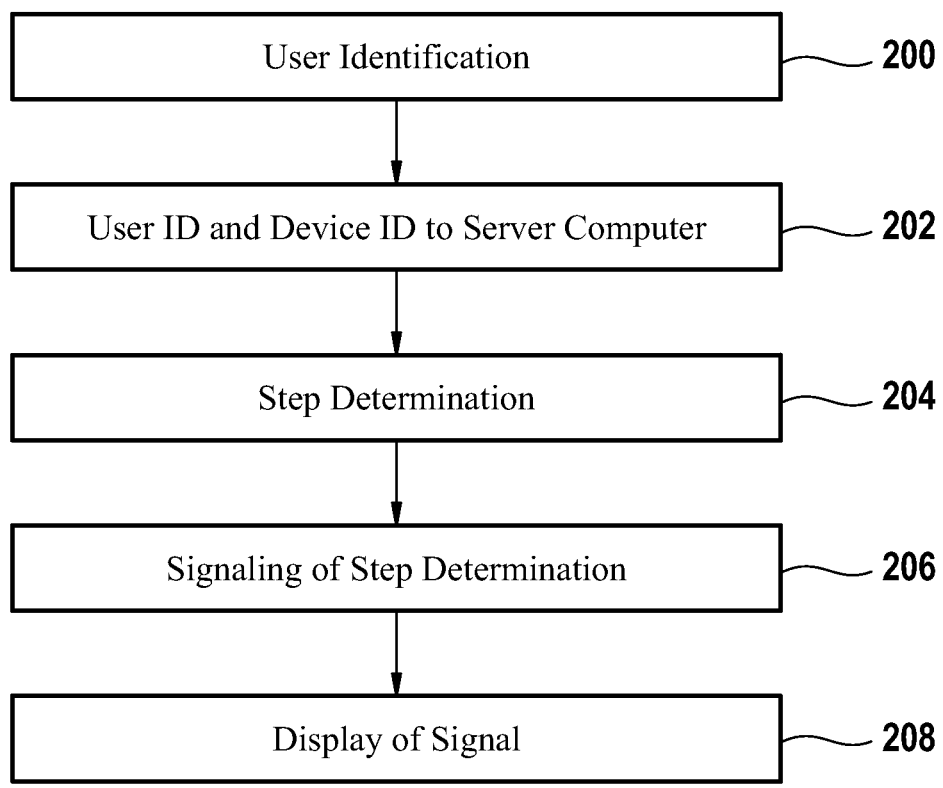
FIG. 2 depicts a flowchart of a method of the present disclosure in accordance with another embodiment of the present disclosure.

FIG. 2 depicts a respective flowchart. In step 200, the user is identified by one of the connected lab devices, such as by connected lab device A. The user identifier and the device identifier of the connected lab device, i.e. connected lab device A, are sent to the server computer in step 202. Next (step 204), the server computer performs a determination of a step of a workflow to be executed by the user identified by the user ID received in step 202.

In step 206, the determined step is signaled from the server computer to the connected lab device identified by the device identifier received in step 202, i.e. connected lab device A. The connected lab device displays a signal in step 208 for informing the user as to the determined step, such as by displaying a text box or a symbol and/or by another kind of visual, haptic and/or acoustic output generated by the connected lab device.

Figure 3:
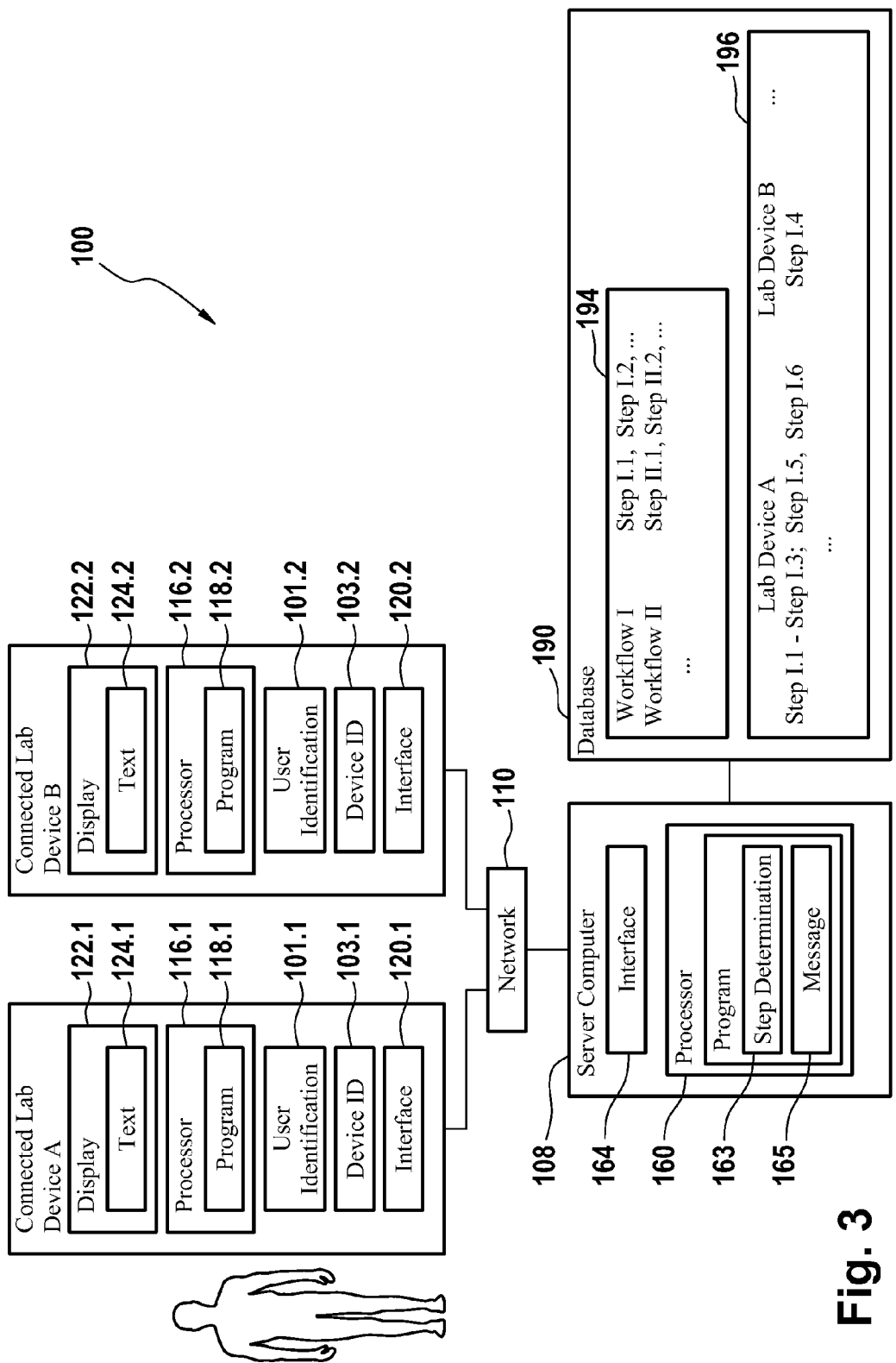
FIG. 3 depicts a block diagram of the analysis system in accordance with yet another embodiment.

FIG. 3 depicts a further embodiment of an analysis system 100. In the embodiment considered here, the storage component 190 is a database that stores a plurality of database tables, such as database tables 194 and 196. The database table 194 contains data for defining a number of workflows and their respective steps, such as a workflow I having steps I.1, I.2, .. . and workflow II having steps II.1, II.2, and the like The database table 196 serves to assign steps of the workflows defined in the database table 194 to the various connected or unconnected lab devices of the analysis system 100. For example, the steps I.1 to I.3 and the steps I.5 and I.6 of the workflow I are assigned to the connected lab device A, whereas the step I.4 of the workflow I is assigned to the connected lab device B. This implies that the step I.4 cannot be executed using connected lab device A as it is not assigned to the connected lab device A in the database table 196 but that the connected lab device B can be used for execution of the step I.4, as this step is assigned to the connected lab device B in the database table 196.

In operation, the server computer 108 receives the user identifier and the device identifier from one of the connected lab devices of the analysis system 100, such as from connected lab device A, as it is the case in the embodiments of FIGS. 1 and 2. By execution of the program module 163, a step of one of the workflows to be executed by the user identified by the user identifier is determined. For example, by execution of the program module 163 it is determined that the step I.4 is to be executed by the user 104 using the database table 194.

After determination of the step to be executed, the database table 196 is accessed in order to determine if the step to be executed is assigned to the lab device identified by the device identifier received by the server computer 108. In the example considered here, this is not the case, as the step I.4 is not assigned to the connected lab device A, but to the connected lab device B in the database table 196. Consequently, the execution of program module 165 is invoked by the program module 163 such that a message is generated.

The message is indicative of the determined step of the workflow to be executed by the user 104, i.e. step I.4, the fact that the connected lab device A cannot be used for execution of that step and/or that the connected lab device B can be used for the execution of the determined step. The message is sent from the server computer 108 to the connected lab device A via the network 110.

Figure 4:
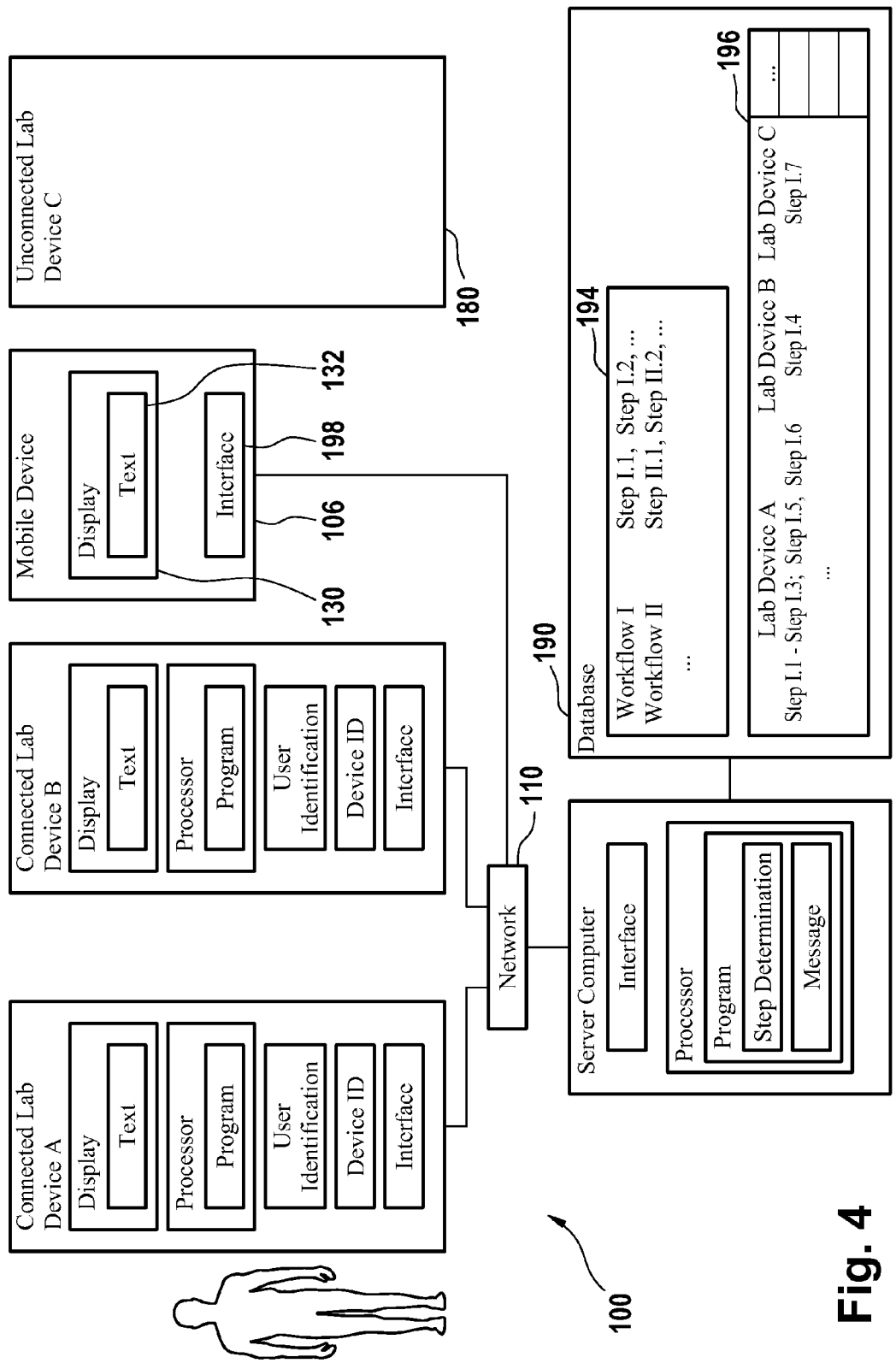
FIG. 4 depicts a block diagram of an analysis system in accordance with yet another embodiment of the present disclosure.

FIG. 4 depicts a further embodiment of the analysis system 100. The analysis system 100 of the embodiment of FIG. 4 has one or more mobile devices, such as mobile device 106. The mobile device 106 has an integrated display 130 for displaying a screen image 132 that may contain a textual or other visual output. Further, the mobile device 106 has a network interface 198 for coupling to the network 110.

In another embodiment, the analysis system 100 has one or more unconnected lab devices, such as unconnected lab device C 180. For example, the unconnected lab device C is a refrigerator for storing reagents that are required for operating the various analyzers of the analysis system 100. A step I.7 can be assigned to the unconnected lab device C in the database table 196.

In operation, the user selects one of the connected lab devices A or B as in the embodiments of FIGS. 1 to 3, such that the server computer 108 receives a user identifier and a device identifier. Alternatively, the user may select the mobile device 106 such that a user identifier and a mobile device identifier are received by the server computer 108 instead. The user identifier and the device identifier are used by the program module 163 for determination of the step of the workflow to be executed by the user 104 by means of the database table 194, as is the case in the embodiments of FIGS. 1 to 3.

For convenience of explanation and without restriction of generality, it is assumed here that the determined step is step I.7. As this step is not assigned to one of the connected lab devices or the mobile device 106, the device identifier received by the server computer 108 is not matching the lab device to which the step I.7 is assigned in the database table 196 such that the program module 163 invokes execution of the program module 165. The program module 165 sends a message to the mobile device 106 indicating the determined step is to be executed by the user 104 and at the unconnected lab device C. In addition, the message may also indicate a location of the unconnected lab device C, such as a laboratory room number in which the unconnected lab device C is located. This position information may also be stored in the database table 196.

Upon receipt of this message on the mobile device 106, the user 104 can walk to the unconnected lab device C for execution of the determined step. After execution is completed, the user 104 may use the mobile device 106 in order to acknowledge completion of the execution which is signaled from the mobile device 106 back to the server computer 108 in order to mark the respective step I.7 as completed in the database table 194.

Figure 5:
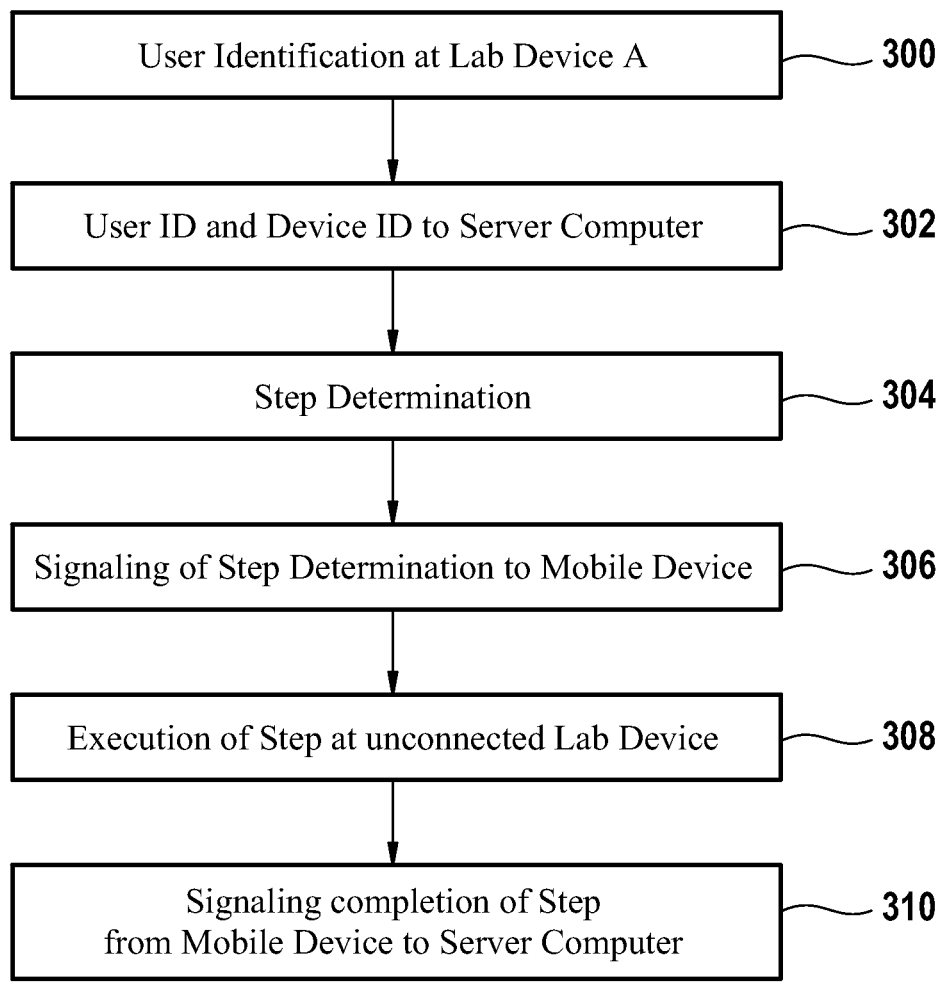
FIG. 5 depicts a flowchart in accordance with another embodiment.

FIG. 5 depicts a respective flowchart of one embodiment. In step 300, the user selects one of the connected lab devices, such as lab device A. The user is identified by the selected lab device A and the user identifier and device identifier of the lab device A are transmitted to the server computer in step 302. In step 304, a step of the workflow to be executed by the user identified by the user identifier is determined by the server computer. If this step is to be executed at an unconnected lab device, such as lab device C, the determined step is signaled from the server computer to the mobile device in step 306. This may include a description of the step to be executed and/or the location of the lab device C.

In step 308, the user executes the determined step at the unconnected lab device and signals completion of the execution of this step from the mobile device to the server computer in step 310 such as by entering an acknowledgement regarding completion of the step into the mobile device.

Figure 6:
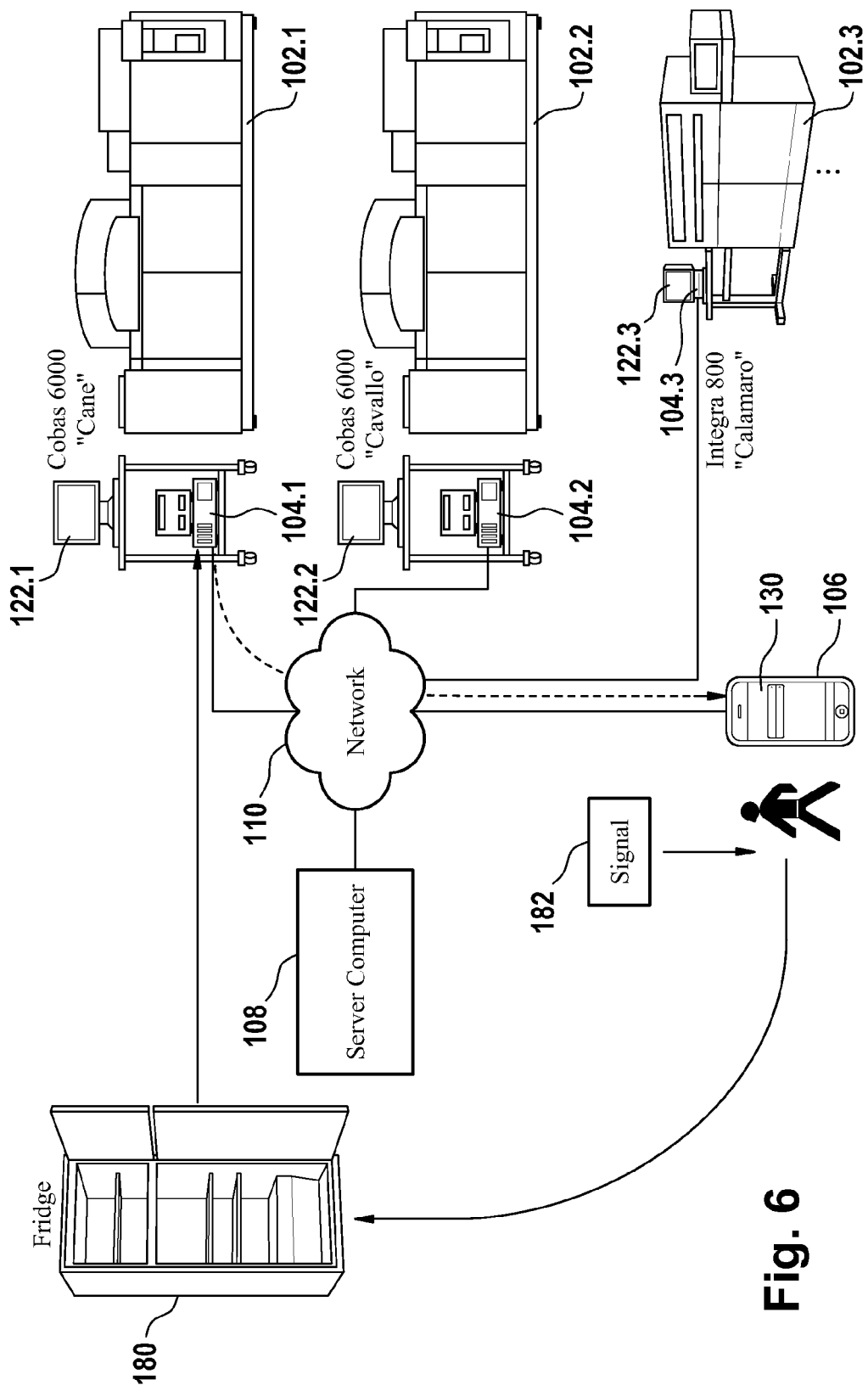
FIG. 6 is illustrative of an embodiment of an analysis system that signals the requirement for refilling a reagent to a user.

FIG. 6 depicts an exemplary embodiment of an analysis system comprising an analyzer 102.1 of the cobas 6000 type having the device identifier 'Cane', analyzer 102.2 of the cobas 6000 type having the device ID 'Cavallo' and analyzer 102.3 of the Integra 800 type having the device ID 'Calamaro'. The analyzer 102.1 and its analyzer control computer 104.1 constitute connected lab device A and the analyzer 102.2 and its analyzer control computer 104.2 constitute connected lab device B (cf. FIGS. 1 to 5). The analysis system further comprises the unconnected lab device 180 which is a refrigerator for storing a stock of reagents.

In operation, one of the analyzers, such as the analyzer 102.1, requires refilling of a reagent. For example, this is sensed by means of a sensor that is coupled to the analyzer control computer 104.1. When the charging level of the reagent of the analyzer 102.1 is below a predefined threshold level, the analyzer control computer 104.1 generates a signal 182 that is sent to the mobile device 106 either directly or through the intermediary of the server computer 108. In one embodiment, the analyzer control computer 104.1 sends the signal 182 to the server computer 108 which then selects the mobile user device 106 for forwarding the signal 182.

FIG. 7 depicts an embodiment of mobile device 106. As depicted, the current screen image 132 displayed on the display 130 of the mobile user device 106 shows a number of due and announced tasks to be executed by the user.

The creation of a task may occur in the following instances:
When one of the analyzers is powered up, it may execute a self-diagnosis. As a result of the self-diagnosis the analyzer or the analyzer control computer coupled to it, may determine that the execution of one or more tasks is required. It may be detected, e.g., by performing the self-diagnosis or by an error message that it is required to refill a reagent, or that a calibration is due.

The user himself or herself recognizes that the execution of a certain task is required and thus selects the respective task to become a due or a current task.

During the ongoing operation of the analysis system, the execution of one or more tasks may become necessary which may be determined automatically by the analysis system or by the user.

There can be various ways to assign tasks to users depending on the implementation:
When an analyzer requires the execution of a certain task, such as a result of its self-diagnosis, the user that attempts to utilize that analyzer is automatically assigned this task.

When the execution of a task becomes necessary as determined automatically by the analysis system or one of the users, this requirement is transmitted to all users or at least a group of the users, as a broadcast or a multicast message, such that one of the users can select that task to become his or her due or current task.

Certain tasks can be pre-assigned to a specific user or user group.

Alternative, the assignment of tasks to users can be implemented by means of the workflow management system.

In the embodiment considered here, the current task that is currently selected by the user is marked by (*). Hence 'Prepare: Cavallo' is the current task.

Due to the signal 182 (cf. FIG. 6) an additional due task appears on the display 132, which is 'Refill Reagents: Cane'. The user can interrupt the execution of the current task 'Prepare: Cavallo' for selection of 'Refill Reagents: Cane' to become the current task or the user may complete the current task before selecting the next task to become the current task which is within the user's discretion. After the user's selection of 'Refill Reagents: Cane' to become the current task the display screen 132 of FIG. 8 is shown.

When the user selects 'Refill Reagents: Cane' to become the current task, the server computer 108 reads analyzer status information for at least Cane or all other available analyzers from the database 166 and provides the retrieved analyzer status information to the mobile user device 106 where the screen image 132 is generated and displayed. In the embodiment depicted in FIG. 8, the screen image 132 provides an overview to the user regarding the filling levels of the various analyzers of the analysis system.

By selection of the navigation button 184, the user can navigate from the currently selected tree node, to another tree node of the user interface; the selection of the navigation button 184 is signaled from the mobile user device 106 to the server computer 108. In response, the respective screen image 132 is displayed as shown in FIG. 9.

In the example considered here, the screen image 132 shows detailed information regarding the filling level of 'Cane'. The image screen 132 comprises control buttons 186 and 188, which the user may select for entry of commands.

When the user decides to execute the current task directly from the analyzer control computer 104, the screen image 124 is displayed on the monitor 122 in the interactive mode, thus containing the control buttons 186 and 188. In addition, the screen image 128 contains information that is not shown on the screen image 132.

For changing to the analyzer control computer 104, the user may perform a login operation or, if the user is already logged-in, only an unspecific entry operation is required, such as a mouse click. In response, the mobile user device 106 is put into the display mode by the server computer 108. As a result, the control buttons 186 and 188 disappear on the screen image 132 of the mobile user device 106 as shown in FIG. 11.

FIG. 12 depicts the screen image 124 after completion of the execution of the current task, i.e. after the refill of the reagent of Cane has been executed. It is important to note that the context of the current user navigation is preserved despite the completion of the current task.

Figure 13:
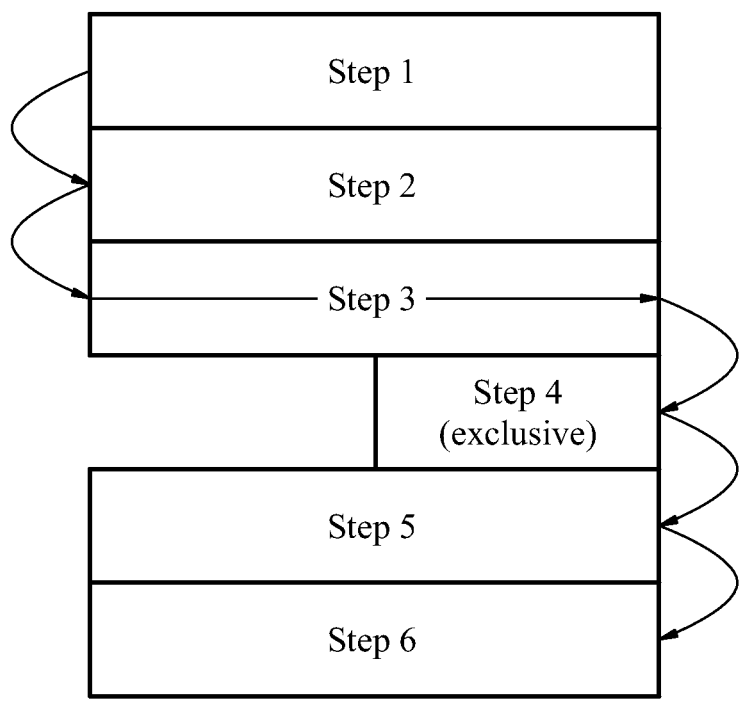
FIG. 13 schematically illustrates the workflow in accordance with another embodiment of the present disclosure.

FIG. 13 illustrates the execution of a task that comprises steps 1 to 6. One of the steps, i.e. step 4, can only be performed from a specific device, such as from the analyzer control computer, but not from the mobile user device, whereas all other steps can be performed both from the mobile user device and from the analyzer control computer. For example, execution of the task is started from the mobile user device. When the task execution reaches completion of step 3, the mobile user device is put into the display mode and the user changes to the analyzer control computer in order to use the analyzer control computer to perform the following steps 4 to 6.

For the purposes of describing and defining the present invention, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters.

It is also noted that recitations herein of "at least one" component, element, etc., should not be used to create an inference that the alternative use of the articles "a" or "an" should be limited to a single component, element, etc.

It is noted that recitations herein of a component of the present disclosure being "programmed" in a particular way, "configured" or "programmed" to embody a particular property, or function in a particular manner, are structural recitations, as opposed to recitations of intended use. More specifically, the references herein to the manner in which a component is "programmed" or "configured" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various inventions described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. An analysis system for analyzing biological samples comprising:
   a first lab device, a second lab device, and a server computer, wherein:
      at least one of the first lab device and the second lab device comprises:
         a user identifier for identifying the user;
         a device identifier for identifying the lab device; and
         an interface component which sends the user identifier and the device identifier to the server computer;
      the server computer comprises:
         a server interface component which receives the user identifier and the device identifier; and
         a processing component which determines a step from a variety of steps of a workflow to be executed by the identified user, wherein said workflow comprises at least two steps which are to be executed at different lab devices, wherein the server interface component is operable to send a signal being indicative of the determined step to the lab device identified by the device identifier, and wherein the server computer further comprises a database which assigns a first set of steps of the workflow to the first lab device and assigns a second set of steps of the workflow to the second lab device.

2. The analysis system of claim 1, wherein the interface component of the lab device is operable to signal completion of the processing component in determining the step of the workflow to the server computer.

3. The analysis system of claim 1, wherein the processing component generates a message when the determined step is not assigned to the identified lab device in the database, and wherein the server interface component sends the message to the identified lab device.

4. The analysis system of claim 3, wherein the message is indicative of at least one of the lab devices to which the determined step is assigned.

5. The analysis system of claim 1, wherein the analysis system further comprises at least one mobile device, wherein the mobile device receives the signal comprising of the determined step of the workflow and the signal comprising at least one of the lab devices to be used for execution of the determined step of the workflow.

6. A computer program product comprising executable instructions which when executed by a system according to claim 1, causes the system to:
   identify a user of at least one of the first lab device and the second lab device;
   send the user identifier and the device identifier of the at least one of the first and second lab devices to the server computer;
   determine a step from a variety of steps of a workflow using the server computer by the user identifier and the device identifier of the at least one of a first and second lab devices; and
   send a signal comprising the determined step from the server computer to at least one of the first and second lab devices.

7. The analysis system of claim 1, wherein the lab device in response to receipt of the signal displays output descriptive of the determined step of the workflow to be executed by the identified user.

8. A method being implemented by an analysis system for analyzing biological samples, the method comprising:
   identifying a user of at least one of a first lab device and a second lab device;
   sending a user identifier and a device identifier of the at least one of the first and second lab devices to a server computer, the server computer assigning from a database a first set of steps of the workflow to the first lab device and assigns a second set of steps of the workflow to the second lab device;
   determining a step from a variety of steps of a workflow using the server computer by the user identifier and the device identifier of the at least one of a first and second lab devices, wherein said determined step is to be executed by the identified user, and wherein said workflow comprises at least two steps which are to be executed at different lab devices; and
   sending a signal comprising of the determined step from the server computer to at least one of the first and second lab devices.

9. The method of claim 8, further comprising:
   identifying the user using the other one of the first and second lab devices;

sending a user identifier and a device identifier of the other one of the first and second lab devices to the server computer;

determining a step of the workflow to be executed by the identified user of the other one of the first and second lab devices; and sending a signal comprising of the determined step of the workflow to the other one of the first and second lab devices.

10. The method of claim 8, further comprising:

receiving the signal on at least one mobile device, wherein the signal comprises the at least one determined step of the workflow and at least one of the lab devices to be used for execution of the at least one step of the workflow.

11. The method of claim 10, wherein the signal comprises position information indicating a geographic or topological location of the at least one lab device to be used for the execution of the at least one determined step.

12. The method of claim 10, wherein the signal comprises one or more steps of the workflow to be executed at an at least one unconnected lab device, wherein the unconnected lab device comprises a lab device that is not coupled to the server computer.

13. The method of claim 10, wherein the signal comprises a priority of the steps of the workflow, and wherein the mobile device or the lab device displays the steps in a prioritized order.

14. The method of claim 10, further comprising signaling completion of the at least one determined step of the workflow from the mobile device to the server computer.

15. The method of claim 14, further comprising executing the determined step of the workflow at an unconnected lab device.

16. A method being implemented by an analysis system for analyzing biological samples, the method comprising:

identifying a user by at least one of a first lab device and a second lab device, said second lab device being separate from said first lab device;

sending a user identifier and a device identifier of the at least one of the first and second lab devices to a server computer to which the first lab device and the second lab device are networked, the server computer assigning from a database a first set of steps of the workflow to the first lab device and assigns a second set of steps of the workflow to the second lab device;

determining a step from a variety of steps of a workflow with the server computer using the user identifier and the device identifier, wherein said workflow comprises at least two steps which are to be executed at different ones of the first and second lab devices for maintenance or operation of the analysis system to analyze the biological samples;

sending a signal comprising the determined step from the server computer to at least one of the first and second lab devices;

receiving the signal on at least one mobile device, wherein the signal comprises the at least one determined step of the workflow, at least one of the lab devices to be used for execution of the at least one step of the workflow by the identified user, position information indicating a geographic or topological location of the lab device to be used for the execution of the at least one determined step by the identified user, and one or more steps of the workflow to be executed at an unconnected lab device by the identified user, and wherein the unconnected lab device comprises a lab device that is not coupled to the server computer.

17. The method of claim 16, further comprising displays on the mobile device output descriptive of the determined step of the workflow to be executed on the lab device by the identified user in response to receipt of the signal.

* * * * *

UNITED STATES PATENT AND TRADEMARK OFFICE
CERTIFICATE OF CORRECTION

PATENT NO. : 8,511,549 B2  
APPLICATION NO. : 12/883271  
DATED : August 20, 2013  
INVENTOR(S) : Anton Steimle et al.

Page 1 of 1

It is certified that error appears in the above-identified patent and that said Letters Patent is hereby corrected as shown below:

In the Specification

Col. 5, Line 27, "methods described" should read --methods are described--;

Col. 5, Line 50, "Internet protocol (IP)" should read --Internet Protocol (IP)--; and Col. 9, Line 52, "Alternative" should read --Alternatively--.

Signed and Sealed this  
Twenty-fourth Day of June, 2014

Michelle K. Lee  
*Deputy Director of the United States Patent and Trademark Office*